US011699304B2

(12) United States Patent
Sakamoto et al.

(10) Patent No.: US 11,699,304 B2
(45) Date of Patent: Jul. 11, 2023

(54) IMAGING DEVICE AND IMAGING METHOD

(71) Applicant: NEC Corporation, Tokyo (JP)

(72) Inventors: Takahiro Sakamoto, Tokyo (JP); Masaki Kuroiwa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/295,112

(22) PCT Filed: Nov. 18, 2019

(86) PCT No.: PCT/JP2019/045040
§ 371 (c)(1),
(2) Date: May 19, 2021

(87) PCT Pub. No.: WO2020/105578
PCT Pub. Date: May 28, 2020

(65) Prior Publication Data
US 2022/0019825 A1   Jan. 20, 2022

(30) Foreign Application Priority Data
Nov. 21, 2018   (JP) .................................. 2018-218343

(51) Int. Cl.
*G06V 40/60* (2022.01)
*G06V 40/12* (2022.01)
(Continued)

(52) U.S. Cl.
CPC ............ *G06V 40/67* (2022.01); *G06T 11/001* (2013.01); *G06V 10/143* (2022.01);
(Continued)

(58) Field of Classification Search
CPC .... G06V 40/67; G06V 10/255; G06V 10/993; G06V 20/00; G06V 40/1365;
(Continued)

(56) References Cited

U.S. PATENT DOCUMENTS 8,270,729 B2   9/2012  Saijo et al.
2001/0026632 A1   10/2001  Tamai
(Continued)

FOREIGN PATENT DOCUMENTS

JP   2001-273498 A   10/2001
JP   2002222424 A   8/2002
(Continued)

OTHER PUBLICATIONS

International Search Report of PCT Application No. PCT/JP2019/045040 dated Feb. 10, 2020.
(Continued)

*Primary Examiner* — Jacinta M Crawford
*Assistant Examiner* — Andrew Shin

(57) ABSTRACT

An imaging device includes: an imaging portion that captures an image of a portion of a living body to take in the image; a display portion that displays first and second display images with being superimposed on each other, the first display image being based on the taken-in image, the second display image including guidance regarding a way to place the portion of the living body in a prescribed position; a determination portion that determines whether the portion of the living body is placed in the prescribed position; and a control portion that, until it is determined that the portion of the living body is placed in the prescribed position, causes the imaging portion to newly capture and take in a new image of the portion of the living body and causes the display portion to display an image based on the new taken-in image.

5 Claims, 8 Drawing Sheets

(51) Int. Cl.
*G06T 11/00* (2006.01)
*G06V 10/143* (2022.01)

(52) U.S. Cl.
CPC ...... *G06V 40/1365* (2022.01); *G06V 40/1394* (2022.01); *G06T 2207/10048* (2013.01)

(58) Field of Classification Search
CPC .............. G06V 40/1394; G06V 10/143; G06T 11/001; G06T 2207/10048; A61B 5/1172
See application file for complete search history.

(56) References Cited

U.S. PATENT DOCUMENTS

| | | | |
|---|---|---|---|
| 2003/0091724 A1 | 5/2003 | Mizoguchi | |
| 2005/0047632 A1 | 3/2005 | Miura et al. | |
| 2007/0201733 A1 | 8/2007 | Hara | |
| 2008/0112597 A1 | 5/2008 | Asano | |
| 2017/0061647 A1* | 3/2017 | Starner | G06V 40/67 |

FOREIGN PATENT DOCUMENTS

| | | |
|---|---|---|
| JP | 2005-071118 A | 3/2005 |
| JP | 2006026427 A | 2/2006 |
| JP | 2007226746 A | 9/2007 |
| JP | 2008123207 A | 5/2008 |
| JP | 2009211357 A | 9/2009 |
| WO | 2013/020577 A2 | 2/2013 |
| WO | 2014/119503 A1 | 8/2014 |
| WO | 2015194017 A1 | 12/2015 |
| WO | 2017179181 A1 | 10/2017 |

OTHER PUBLICATIONS

E. Tabassi et al., "Fingerprint Image Quality", NISTIR 7151 Aug. 2004, National Institute of Standards and Technology, Aug. 19, 2004, pp. 1-72.

Extended European Search Report for EP Application No. 19886506.5 dated Dec. 15, 2021.

JP Office Action for JP Application No. 2020-558369, dated May 24, 2022 with English Translation.

Japanese Office Action for JP Application No. 2020-558369 dated Nov. 1, 2022 with English Translation.

* cited by examiner

IMAGING DEVICE AND IMAGING METHOD

This application is a National Stage Entry of PCT/JP2019/045040 filed on Nov. 18, 2019, which claims priority from Japanese Patent Application 2018-218343 filed on Nov. 21, 2018, the contents of all of which are incorporated herein by reference, in their entirety.

TECHNICAL FIELD

The example embodiments relate to an imaging device and an imaging method.

BACKGROUND ART

Patent Document 1 shows an example of a personal authentication device that identifies an individual by using a finger vein pattern. In the personal authentication device described in Patent Document 1, in order to provide guidance regarding the correct way of inserting a finger into the imaging portion, an image showing the image capture state of the finger and a contour guide that serves as a guide for aligning the contour of the finger are displayed in an overlapped state on a monitor. In addition, information indicating how the user should correct the finger state is displayed on this monitor using sentences and images. According to the personal authentication device described in Patent Document 1, by the user correctly performing the registration work according to the guidance on the screen, the work performed by the administrator at the time of registration will be reduced.

PRIOR ART DOCUMENTS

Patent Documents

[Patent Document 1] Japanese Unexamined Patent Application, First Publication No. 2006-26427

SUMMARY OF THE INVENTION

Problem to be Solved by the Invention

In the personal authentication device described in Patent Document 1, the correct way of inserting a finger into the imaging portion is indicated by sentences (text) and figures. For that reason, for example, if the user cannot comprehend the language of the sentences, the guidance may not be understood or the effect of the guidance may be reduced. Therefore, there is a problem in which an object such as a finger sometimes cannot be placed at the correct imaging position.

An example object of the example embodiment is to provide an imaging device and an imaging method capable of solving the above-mentioned problems.

Means for Solving the Problem

One example aspect of the present invention is an imaging device including: an imaging portion that captures an image of a portion of a living body to take in the image; a display portion that displays a first display image and a second display image with being superimposed on each other, the first display image being based on the image taken in by the imaging portion, the second display image including guidance regarding a way to place the portion of the living body in a prescribed position; a determination portion that determines whether the portion of the living body is placed in the prescribed position; and a control portion that, until the determination portion determines that the One example aspect of the example embodiment is an imaging device including: an imaging portion that captures an image of a portion of a living body to take in the image; a display portion that displays a first display image and a second display image with being superimposed on each other, the first display image being based on the image taken in by the imaging portion, the second display image including guidance regarding a way to place the portion of the living body in a prescribed position; a determination portion that determines whether the portion of the living body is placed in the prescribed position; and a control portion that, until the determination portion determines that the portion of the living body is placed in the prescribed position, causes the imaging portion to newly capture and take in a new image of the portion of the living body and causes the display portion to display, as the first display image, an image based on the new image taken in by the imaging portion.

Further, one example aspect of the example embodiment is an imaging method including: capturing an image of a portion of a living body to take in the image; displaying a first display image and a second display image with being superimposed on each other, the first display image being based on the taken-in image, the second display image including guidance regarding a way to place the portion of the living body in a prescribed position; determining whether the portion of the living body is placed in the prescribed position; and until it is determined that that the portion of the living body is placed in the prescribed position, newly capturing and taking in a new image of the portion of the living body and displaying, as the first display image, an image based on the new taken-in image.

Effect of the Invention

According to each example aspect of the example embodiments, the user can easily place a portion of a living body (for example, an object) in a prescribed position (for example, a correct imaging position).

EXAMPLE EMBODIMENT

Figure 1:
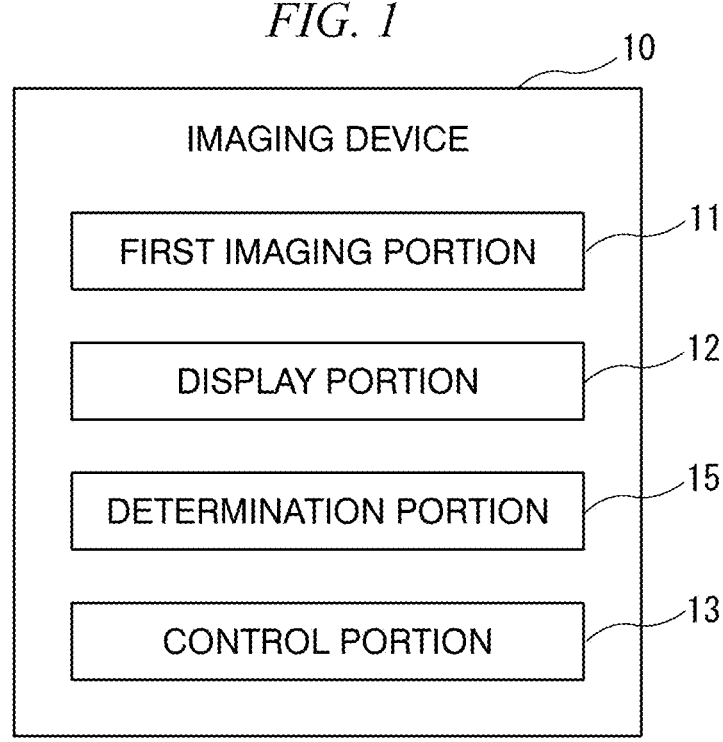
FIG. 1 is a schematic configuration diagram showing a configuration example of an imaging device according to a first example embodiment.

Hereinbelow, example embodiments will be described with reference to the drawings. FIG. 1 is a schematic configuration diagram showing a configuration example of an imaging device according to a first example embodiment. The imaging device 10 shown in FIG. 1 includes an imaging portion 11, a display portion 12, a control portion 13, and a determination portion 15 that supplies an image determination result to the control portion 13. A first imaging portion 11 images an object to be imaged, such as a portion of a living body, placed at a predetermined imaging position. The display portion 12 displays a first display image representing an image of the portion of the living body captured by the imaging portion and a second display image representing an authenticatable area that can be effectively authenticated from the captured image. The determination portion 15 determines whether or not authentication by the first display image displayed on the display portion 12 is possible. The control portion 13, by controlling the first imaging portion 11, the display portion 12, and the determination portion 15, repeats the imaging of a portion of the living body by the first imaging portion 11 to display the first display image of the display portion 12 at the imaged position until the determination portion 15 determines that determination by the first display image is possible.

According to the imaging device 1 shown in FIG. 1, since the user can recognize whether or not the object is correctly placed at the imaging position on the basis of a change in the display mode of the display portion 12, the object can be easily placed in the correct imaging position.

Figure 2:
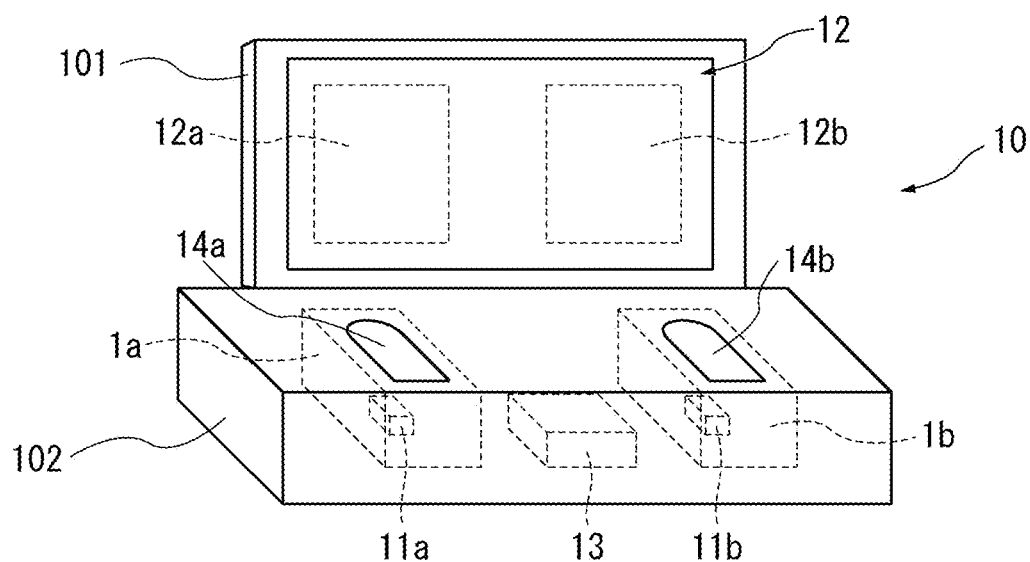
FIG. 2 is a perspective view schematically showing a configuration example of an imaging device 10 according to a second example embodiment.

Next, the imaging device 1 according to a second example embodiment will be described with reference to FIG. 2. FIG. 2 is a perspective view schematically showing a configuration example of the imaging device 10 shown in FIG. 1. In FIG. 2, those configurations corresponding to the configurations shown in FIG. 1 are given the same reference symbols. In the example shown in FIG. 2, the object to be imaged is a fingertip portion (the distal end of a person's finger). One purpose of the imaging device 10 is to capture a fingerprint on the ventral surface of the fingertip portion as a physical feature for biometric authentication. However, the object to be imaged by the imaging device 10 is not limited to a fingertip portion, and may be a palm or the like. That is, one purpose of the imaging device 10 may be to capture another physical feature for biometric authentication such as a palm print. Further, the object of the imaging device 10 is not limited to a part of the body.

In the example shown in FIG. 2, the imaging device 10 includes a housing 101 and a housing 102. The housing 101 is provided with a display portion 12. The housing 102 is provided with two imaging units 1a and 1b and the control portion 13. The imaging unit 1a includes a first imaging portion 11a corresponding to the first imaging portion 11 shown in FIG. 1, and a light source portion and an optical system described later. The imaging unit 1a captures by the first imaging portion 11a a first image representing a fingertip portion, which is an object placed at an imaging position 14a. Similarly to the imaging unit 1a, the imaging unit 1b includes a first imaging portion 11b corresponding to the first imaging portion 11 shown in FIG. 1, and a light source portion and an optical system described later. The imaging unit 1b captures by means of the first imaging portion 11b a first image representing the fingertip portion, which is an object placed at an imaging position 14b. Each first imaging portion 11 may include one imaging portion (camera) to capture one type of first image, or may include two or more imaging portions (cameras) to capture two types of images.

The display portion 12, which is for example a liquid crystal display or an organic electroluminescence display, displays an image in a display area 12a and a display area 12b under the control of the control portion 13. Specifically, the display portion 12 displays in the display area 12a a first display image representing the fingertip portion placed at the imaging position 14a, and a second display image showing guidance on how to place the fingertip portion at the imaging position 14a. The first display image is an image based on the first image obtained by the first imaging portion 11a imaging the fingertip portion placed at the imaging position 14a. Further, the display portion 12 displays in the display area 12b the first display image and the second display image showing guidance on how to place the fingertip portion at the imaging position 14b. The first display image is an image based on the first image obtained by the first imaging portion 11b imaging the fingertip portion placed at the imaging position 14b.

The control portion 13 acquires the first image captured by the first imaging portion 11a, and determines whether or not the fingertip portion is correctly placed at the imaging position 14a based on the acquired first image. The control portion 13 changes the display mode in the display area 12a of the display portion 12 depending on whether a case of the fingertip portion being correctly placed or a case of the fingertip portion being not correctly placed. Further, the control portion 13 acquires the first image captured by the first imaging portion 11b, and determines whether or not the fingertip portion is correctly placed at the imaging position 14b based on the acquired first image. The control portion 13 changes the display mode in the display area 12b of the display portion 12 depending on whether a case of the fingertip portion being correctly placed or a case of the fingertip portion being not correctly placed.

The imaging device 10 shown in FIG. 2 includes two imaging positions 14a and 14b, whereby, for example, fingerprints of one finger of both hands can be simultaneously imaged. In the following, when it is not necessary to distinguish between the imaging position 14a and the imaging position 14b, the imaging unit 1a and the imaging unit 1b, the display area 12a and the display area 12b, and the first imaging portion 11a and the first imaging portion 11b, they shall be collectively referred to by the reference symbols of the imaging position 14, the imaging unit 1, the display area 12, and the first imaging portion 11, respectively.

Figure 3:
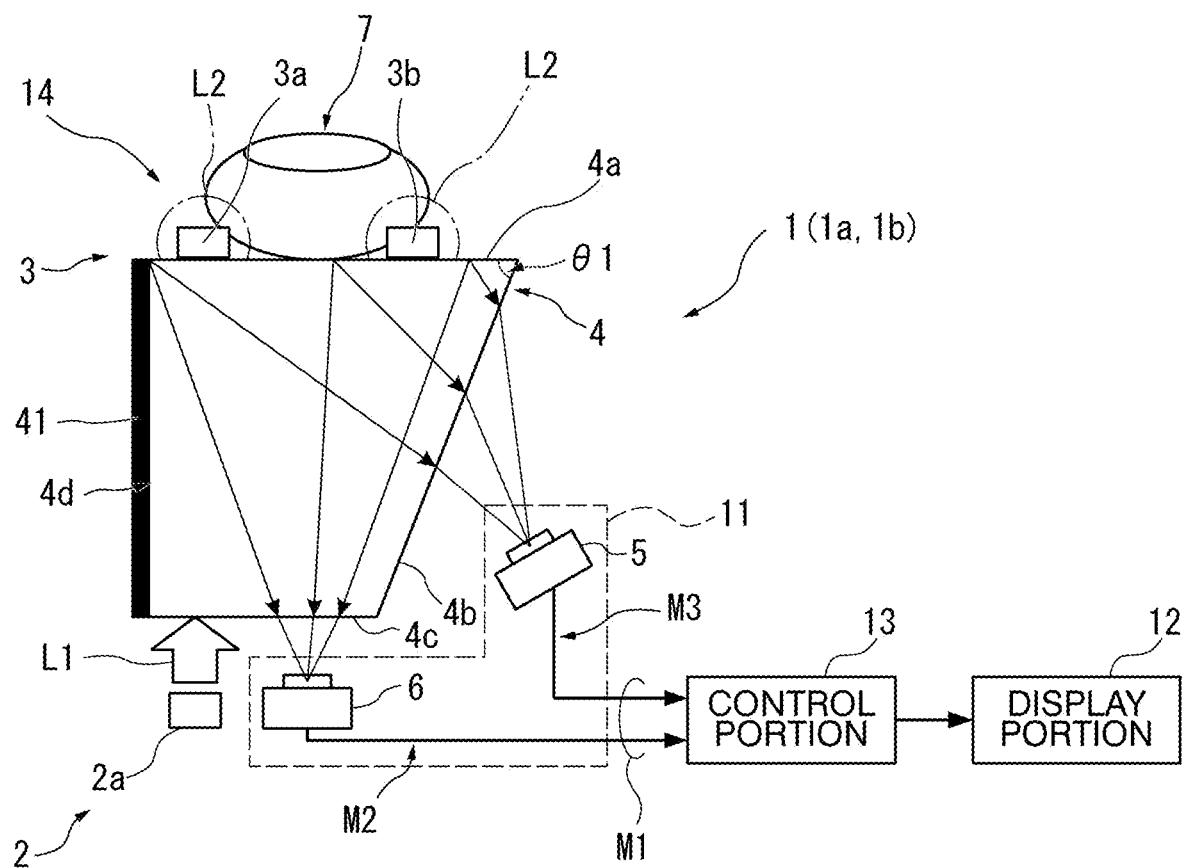
FIG. 3 is a schematic view showing a configuration example of an imaging unit 1 according to the second example embodiment.

Next, a configuration example of the imaging unit 1 shown in FIG. 2 will be described with reference to FIGS. 3 to 8B. FIG. 3 is a front view schematically showing a detailed configuration example of the imaging unit 1 shown in FIG. 2. In FIG. 3, those configurations corresponding to the configurations shown in FIG. 2 are denoted by the same reference symbols. In the example shown in FIG. 3, the imaging position 14 is provided on a contact surface 4a of the optical element 4. A fingertip portion 7 is placed at the imaging position 14.

In the example shown in FIG. 3, the imaging unit 1 includes a first light source portion 2, a second light source portion 3, an optical element 4, and a first imaging portion 11. The first imaging portion 11 includes a second imaging portion 6 and a third imaging portion 5. Further, a first image M1 that is an image captured by the first imaging portion 11 includes a second image M2 that is an image captured by the second imaging portion 6 and a third image M3 that is an image captured by the third imaging portion 5.

The display portion 12 displays the first display image representing the fingertip portion 7, which is the object, based on the second image M2. The control portion 13 determines whether or not the fingertip portion 7, which is the object, is correctly placed at the imaging position 14 based on the third image M3.

In the example shown in FIG. 3, the optical element 4 is a prism. The optical element (prism) 4 has the contact surface 4a, an intersection surface 4b, an opposing surface 4c that opposes the contact surface 4a, and a surface 4d. The contact surface 4a is the surface on which the fingertip portion 7, which is the object, comes into contact. The intersection surface 4b intersects the contact surface 4a at a predetermined angle θ1. The opposing surface 4c opposes the contact surface 4a. The surface 4d opposes the intersecting surface 4b. In this example, the optical element (prism) 4 is a polyhedron (for example, a hexahedron) having a refractive index different from that of air, and can be formed of, for example, glass, crystal, or the like. In the example shown in FIG. 3, the angle θ1 is an acute angle. The opposing surface 4c may or may not be parallel to the contact surface 4a. A black plate 41 is attached to the surface 4d in order to enhance the contrast of the image. However, the surface 4d may be coated with black paint or the like instead of the black plate 41. The optical element 4 is not limited to a prism. The optical element 4 may be a lens, a reflector, an optical fiber, or a combination thereof capable of guiding light rays from a light source to the object and guiding light rays reflected by the object to the imaging unit 1.

In the arrangement of the second imaging portion 5 shown in FIG. 3, the angle θ1 is an acute angle. However, the angle θ1 is not limited to an acute angle, and the angle θ1 may be an obtuse angle or a right angle depending on the arrangement of the imaging portions, for example, when the second imaging portion 5 is arranged below.

The first light source portion 2 is provided below the optical element 4 and has a visible light LED 2a such as a white LED (light emitting diode). The first light source portion 2, that is, the visible light LED 2a, outputs a first light L1. In this case, the first light L1 contains a large amount of visible light components having a wavelength of about 380 to 800 nm. Further, in the example shown in FIG. 3, the first light L1 is irradiated from the opposing surface 4c side of the optical element 4 (prism) to the fingertip portion 7, which is the object.

The second light source portion 3 is provided on the contact surface 4a of the optical element 4 and has a plurality of infrared LEDs 3a and 3b. The second light source portion 3, that is, the plurality of infrared LEDs 3a and 3b, outputs the second light L2 having a wavelength longer than that of the first light L1. The second light L2 contains a large amount of infrared components having a wavelength of about 800 nm to 1000 nm. Further, in the example shown in FIG. 3, the second light L2 is irradiated from the peripheral portion on the contact surface 4a to the fingertip portion 7, which is the object.

The second imaging portion 6 images the fingertip portion 7, which is the object, from the opposing surface 4c side. The second imaging portion 6 has an imaging element such as a CMOS (complementary metal oxide semiconductor) image sensor or a CCD (charge coupled device) image sensor, and an infrared cut filter. The second imaging portion 6 converts the visible light component of the input light into an image signal and outputs the image signal as the second image M2 to the control portion 13. The second imaging portion 6 has low sensitivity to the second light L2. That is, the second imaging portion 6 has a predetermined sensitivity to the first light L1 and does not have a predetermined sensitivity to the second light L2. However, the second imaging portion 6 may not have an infrared cut filter. In this case, for example, the same effect as when the infrared cut filter is provided may be obtained by image processing or the like.

The third imaging portion 5 images the fingertip portion 7, which is the object, from the intersection surface 4b side. The third imaging portion 5 has an imaging element such as a CMOS image sensor or a CCD image sensor. The third imaging portion 5 converts the visible light component and the infrared component of the input light into an image signal and outputs the image signal as the third image M3 to the control portion 13. The third imaging portion 5 is highly sensitive to the first light L1 and the second light L2. That is, the third imaging portion 5 has a predetermined sensitivity to the first light L1 and the second light L2.

Figure 4:
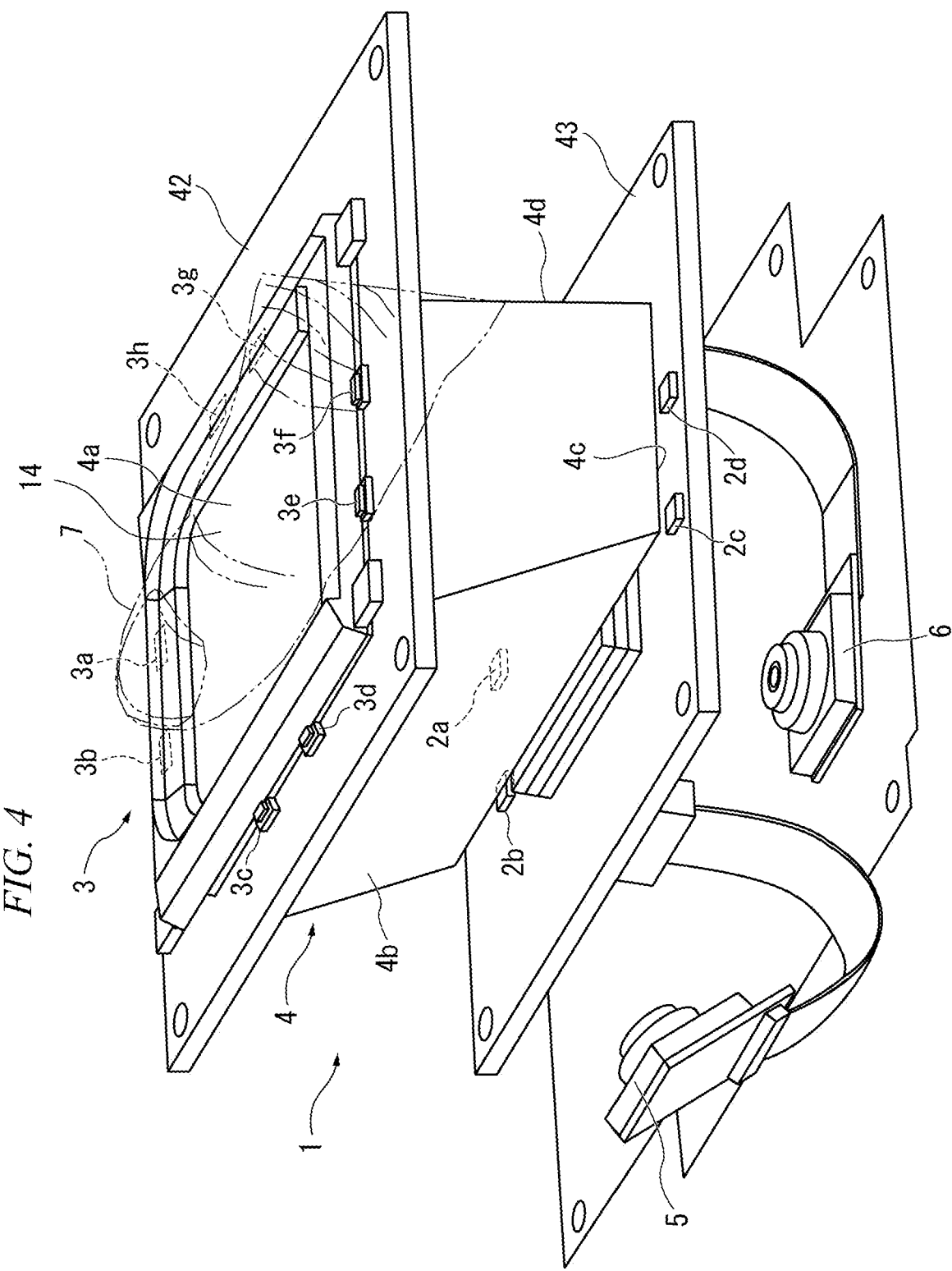
FIG. 4 is a perspective view showing a configuration example of the imaging unit 1 shown in FIG. 3.

FIG. 4 is a perspective view schematically showing an arrangement example of each part of the imaging unit 1 shown in FIG. 3. In FIG. 4, those configurations corresponding to the configurations shown in FIG. 3 are denoted by the same reference symbols. In the imaging unit 1 shown in FIG. 4, the first light source portion 2 is composed of four white LEDs 2a, 2b, 2c and 2d arranged on the opposing surface 4c side of the optical element (prism) 4. The four white LEDs 2a, 2b, 2c and 2d are mounted on a substrate 43. The substrate 43 supports the optical element (prism) 4 from the opposing surface 4c side to fix them. Further, the second light source portion 3 is composed of eight infrared LEDs 3a, 3b, 3c, 3d, 3e, 3f, 3g and 3h arranged in the peripheral portion on the contact surface 4a of the optical element (prism) 4. The eight infrared LEDs 3a, 3b, 3c, 3d, 3e, 3f, 3g and 3h are mounted on a substrate 42. The substrate 42 supports the optical element (prism) 4 from the contact surface 4a side to fix them. The number of LEDs is not limited to the example shown in FIG. 4.

Figure 5:
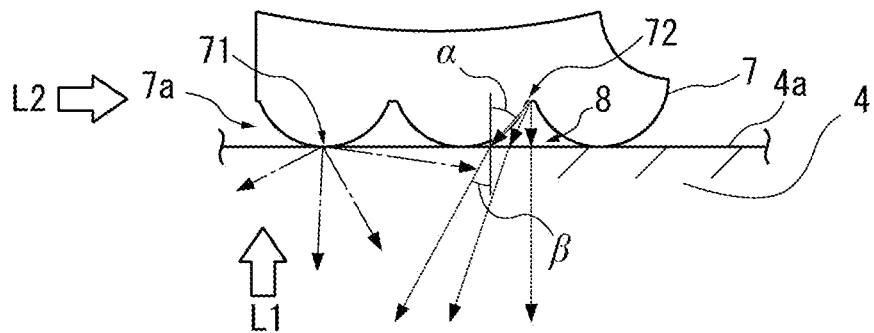
FIG. 5 is a schematic diagram for explaining an operation example of the imaging unit 1 shown in FIG. 3.
Figure 6:
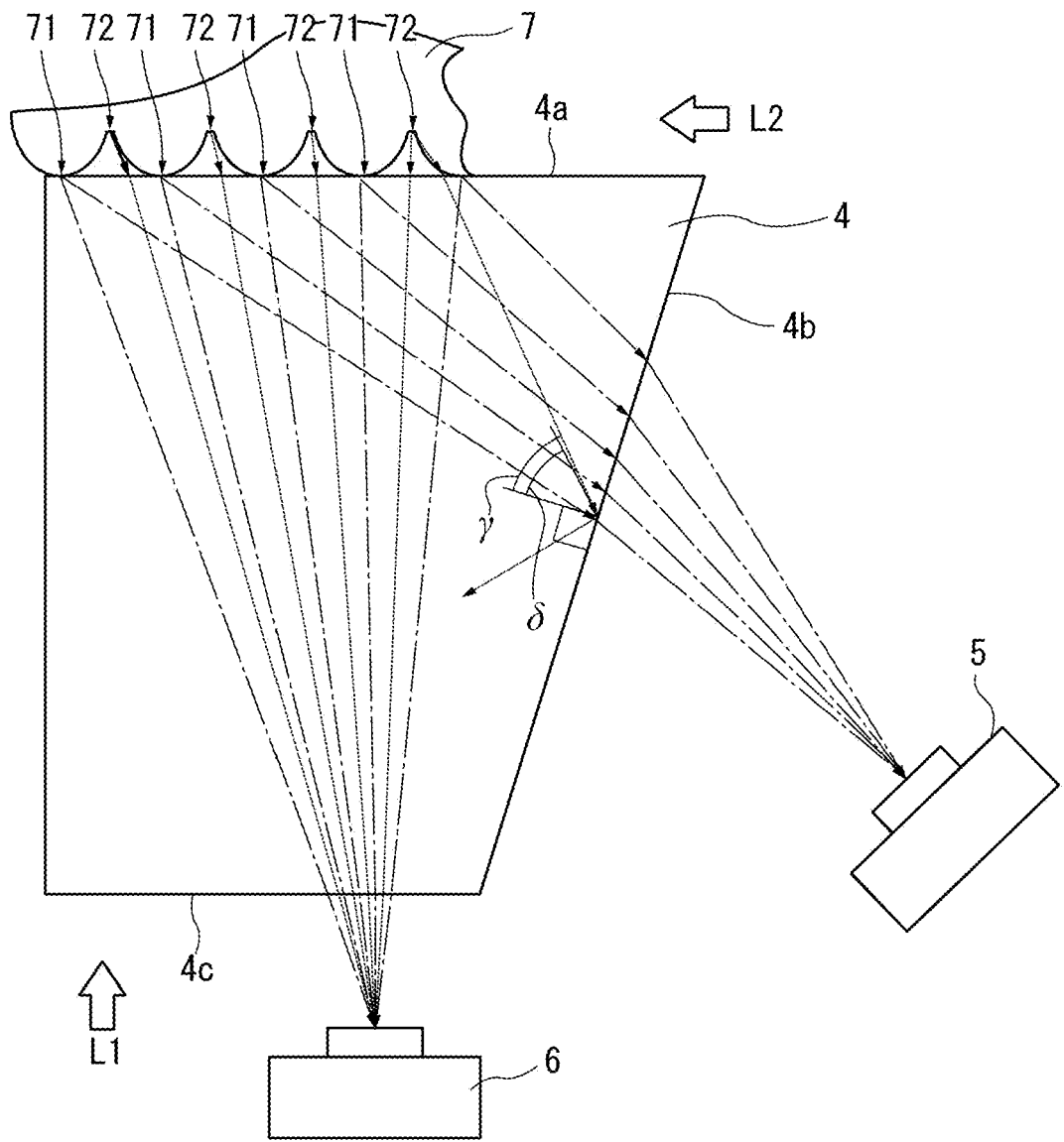
FIG. 6 is a schematic diagram for explaining an operation example of the imaging unit 1 shown in FIG. 3.

Next, each optical path in the optical element (prism) 4 shown in FIG. 3 will be described with reference to FIGS. 5 and 6. FIG. 5 is an enlarged schematic view showing the contact surface 4a and the fingertip portion 7 shown in FIG. 3. FIG. 6 is a schematic view showing an enlarged view of the optical element (prism) 4 and the fingertip portion 7 shown in FIG. 3. As described above, one object of the imaging unit 1 of the second example embodiment is to capture the image of a fingerprint, which is one of the biological features. A fingerprint is composed of a combination of projecting and recess (valley line portions 72 and ridge line portions 71) on the ventral surface 7a of the fingertip portion 7. The first light L1 output by the first light source portion 2 is reflected by the ridge line portions 71 and the valley line portions 72 placed on the contact surface 4a to be incident on the optical element (prism) 4. Further, the second light L2 output by the second light source portion 3 passes through the fingertip portion 7, is emitted from the ridge line portions 71 and the valley line portions 72 placed on the contact surface 4a, and is incident on the optical element (prism) 4 from the contact surface 4a.

As shown in FIG. 5, the ridge line portion 71 of the fingertip portion 7 is in contact with the contact surface 4a.

For this reason, the refractive index of the light incident from the ridge line portion 71 or reflected by the ridge line portion 71 is substantially the same as the refractive index of the optical element (prism) 4 (glass or the like). Therefore, the light emitted from the ridge line portion 71 or reflected by the ridge line portion 71 can be regarded as the same as the light reflected by the contact surface 4a. That is, this light is radiated substantially evenly in almost all directions in the optical element (prism) 4 as indicated by the arrows of the dashed lines, and can reach all the regions below the contact surface 4a.

On the other hand, the valley line portion 72 is not in contact with the contact surface 4a, and so there is an air layer 8 between the valley line portion 72 and the contact surface 4a. Accordingly, the light emitted from the valley line portion 72 or the reflected light at the valley line portion 72 is incident on the contact surface 4a via the air layer 8. Here, the refractive index of air is 1.0. The refractive index of glass is generally around 1.5, being in the range of 1.3 to 2.0. The refractive index of water and skin is 1.3 to 1.4. As described above, since the refractive indices differ, the refraction phenomenon of the emitted light and the reflected light from the valley line portion 72 is different from the emitted light and the reflected light of the ridge line portion 71. Specifically, the emitted light and the reflected light from the valley line portion 72 are not radiated in all directions. Further, since the refraction angle $\beta$ is smaller than the incident angle $\alpha$, the light emitted from the valley line portion 72 and the light reflected by the valley line portion 72 are biased toward light heading downward in the optical element (prism) 4 as shown by the arrows of the dashed lines.

As described with reference to FIG. 5, the light from the ridge line portion 71 is radiated substantially evenly from the contact surface 4a in all directions, and the light from the valley line portion 72 is radiated in a manner biased downward from the contact surface 4a. Further, the light from the valley line portion 72 is radiated in a manner biased downward. Therefore, as shown in FIG. 6, the incident angle $\gamma$ of the light from the valley line portion 72 onto the intersection surface 4b is larger than that of the light from the ridge line portion 71. Therefore, as compared with the case of the light from the ridge line portion 71, the proportion of the incident angle $\gamma$ of the light from the valley line portion 72 exceeding the critical angle $\delta$ becomes larger. Therefore, as compared with the case of the light from the ridge line portion 71, the ratio of the light from the valley line portion 72 being totally reflected by the intersecting surface 4b is larger. Therefore, the light from the ridge line portion 71 reaches the third imaging portion 5 more than the light from the valley line portion 72. Here, the third imaging portion 5 images the fingertip portion 7 from the intersection surface 4b side to obtain the third image M3. Accordingly, in the third image M3, the ridge line portion 71 is bright and the valley line portion 72 is dark, and therefore, the third image M3 is a high-contrast fingerprint image (hereinafter referred to as a high-contrast image). Further, when imaging the fingertip portion 7, the first light L1 is irradiated to the fingertip portion 7 from the opposing surface 4c side, while the second light L2 is emitted to the fingertip portion 7 from the peripheral portion of the contact surface 4a. For this reason, the peripheral portion of the fingertip portion 7, which is difficult for the first light L1 to reach, can be brightened by the second light L2. Therefore, the third imaging portion 5 can image a fingerprint in a state where the entire fingerprint is appropriately illuminated. Accordingly, according to the second example embodiment, it is possible to increase the contrast across the entire fingerprint image.

On the other hand, the light from the ridge line portion 71 and the light from the valley line portion 72 reach the second imaging portion 6 at a substantially equal ratio as compared with the ratio of reaching the third imaging portion 5. Here, the second imaging portion 6 images the fingertip portion 7 from the opposing surface 4c side to obtain the second image M2. The second image M2 is an image similar to that seen when the fingertip portion 7 placed on the contact surface 4a is directly viewed from the opposing surface 4c. The second image M2 is an image in which the infrared component is suppressed. Accordingly, the image captured by the second imaging portion 6 is a natural image of the fingertip portion 7 (hereinafter termed a natural image). However, as described above, the infrared component need not be suppressed depending on the use of the image captured by the second imaging portion 6.

The high-contrast image (third image M3) captured by the third imaging portion 5 is used, for example, for collating fingerprints. At that time, it is desirable that the third imaging portion 5 capture a fingerprint image of a wider area so that many minutiae are present in the image. In the second example embodiment, since the third imaging portion 5 can capture a fingerprint image having high contrast throughout, for example, the accuracy of fingerprint collation can be easily improved. On the other hand, the natural image (second image M2) captured by the second imaging portion 6 is used, for example, for the purpose of determining whether the finger is fake or genuine. Moreover, the natural image (second image M2) captured by the second imaging portion 6 is used, for example, for displaying the placement state of the fingertip portion 7 at the imaging position 14 on the display portion 12 in a substantially real-time manner.

Figure 7:
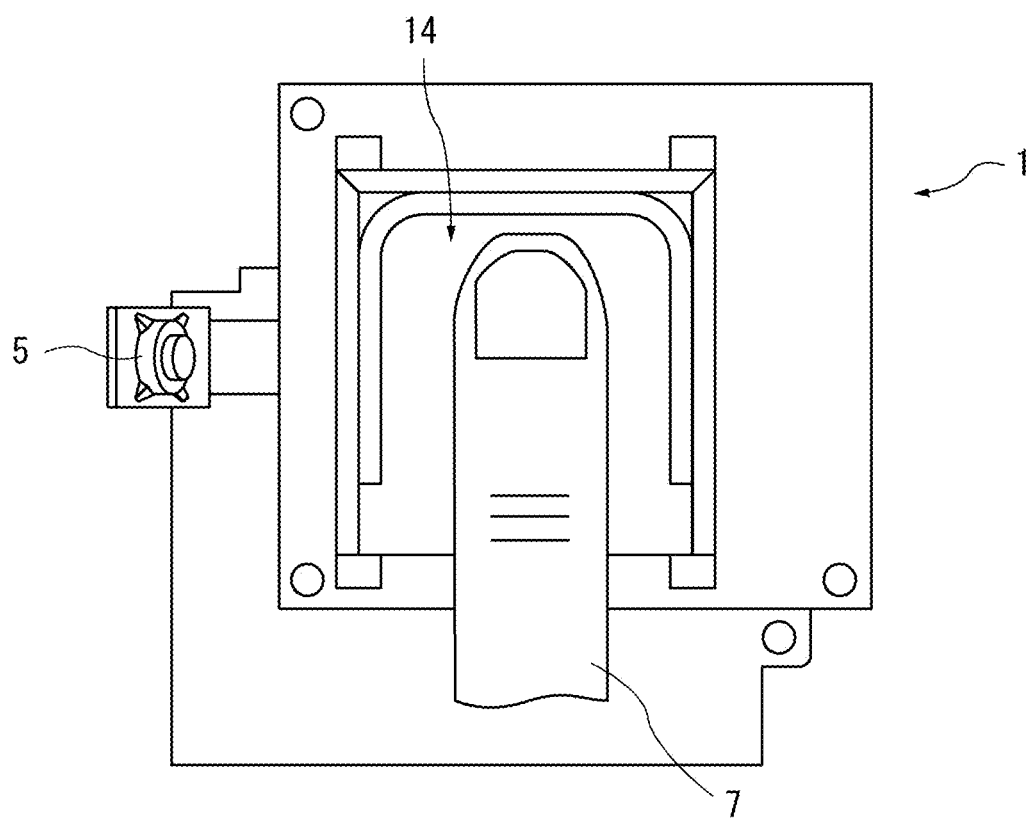
FIG. 7 is a plan view schematically showing a configuration example of the imaging unit 1 shown in FIG. 3.
Figure 8A:
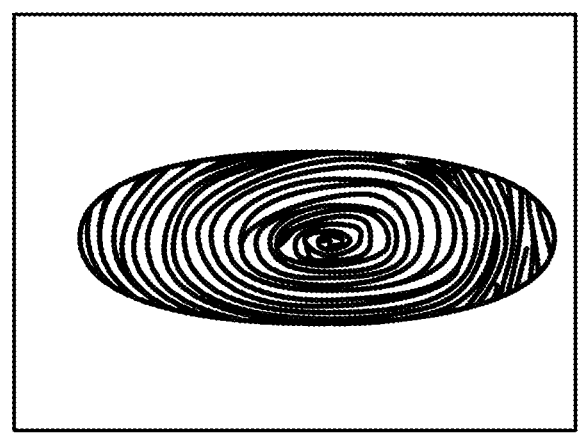
FIG. 8A is a diagram showing an example of an image captured by the imaging unit 1 shown in FIG. 3.
Figure 8B:
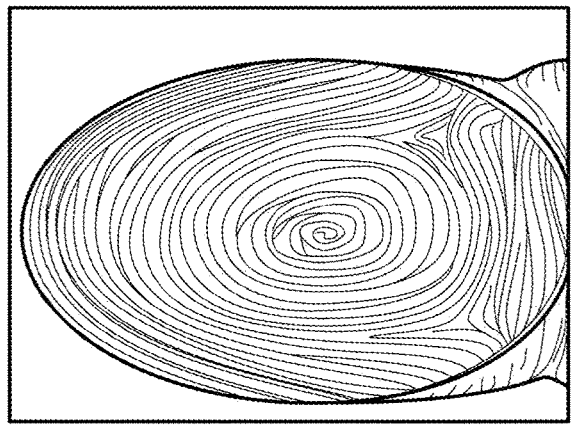
FIG. 8B is a diagram showing an example of an image captured by the imaging unit 1 shown in FIG. 3.

FIG. 7 is a plan view schematically showing an example of the case where the fingertip portion 7 is correctly placed at the imaging position 14 on the imaging unit 1 shown in FIG. 4. FIG. 8A shows an example of the third image M3 captured by the third imaging portion 5. FIG. 8B shows an example of the second image M2 captured by the second imaging portion 6.

Figure 9:
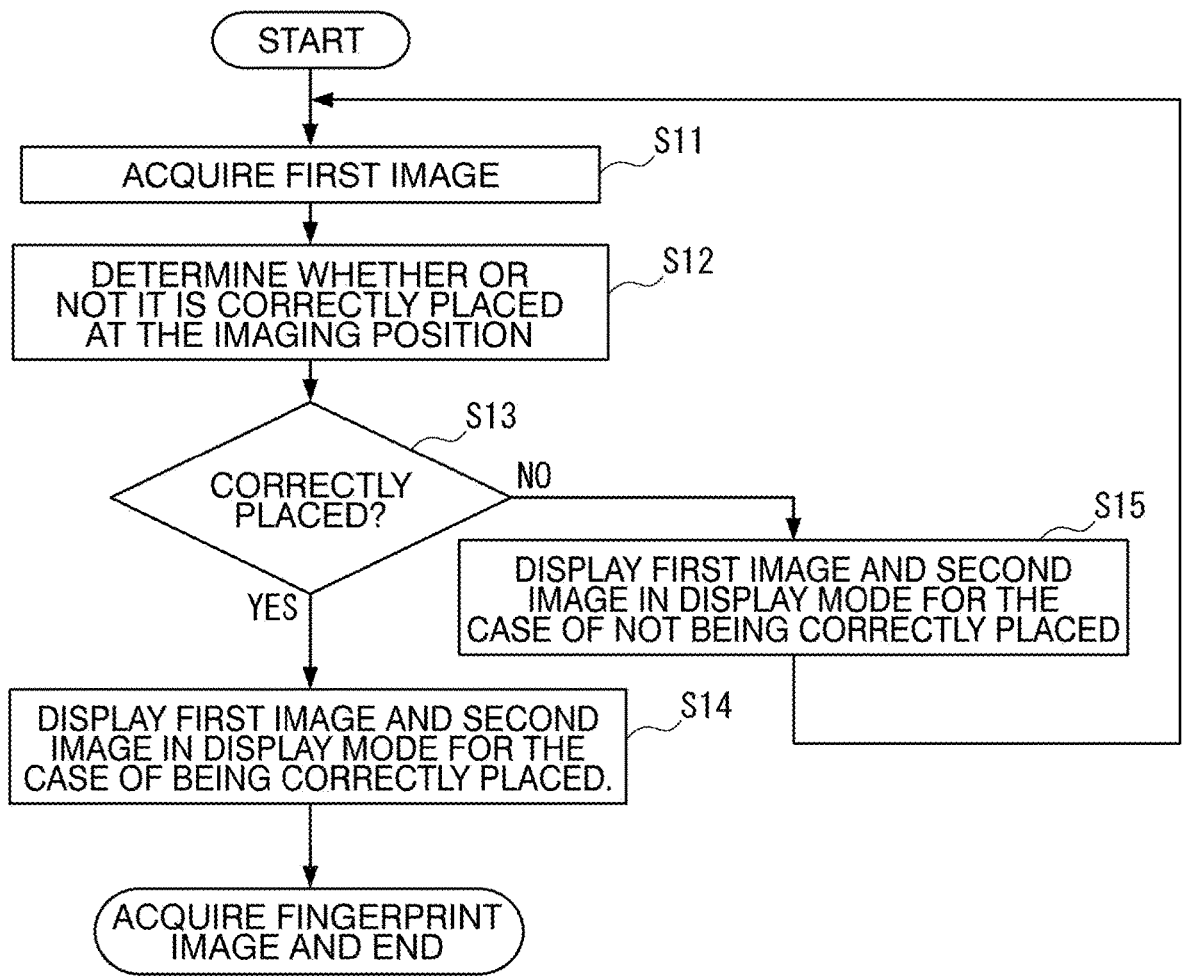
FIG. 9 is a flowchart showing an operation example of the imaging device 1 shown in FIG. 1.
Figure 10:
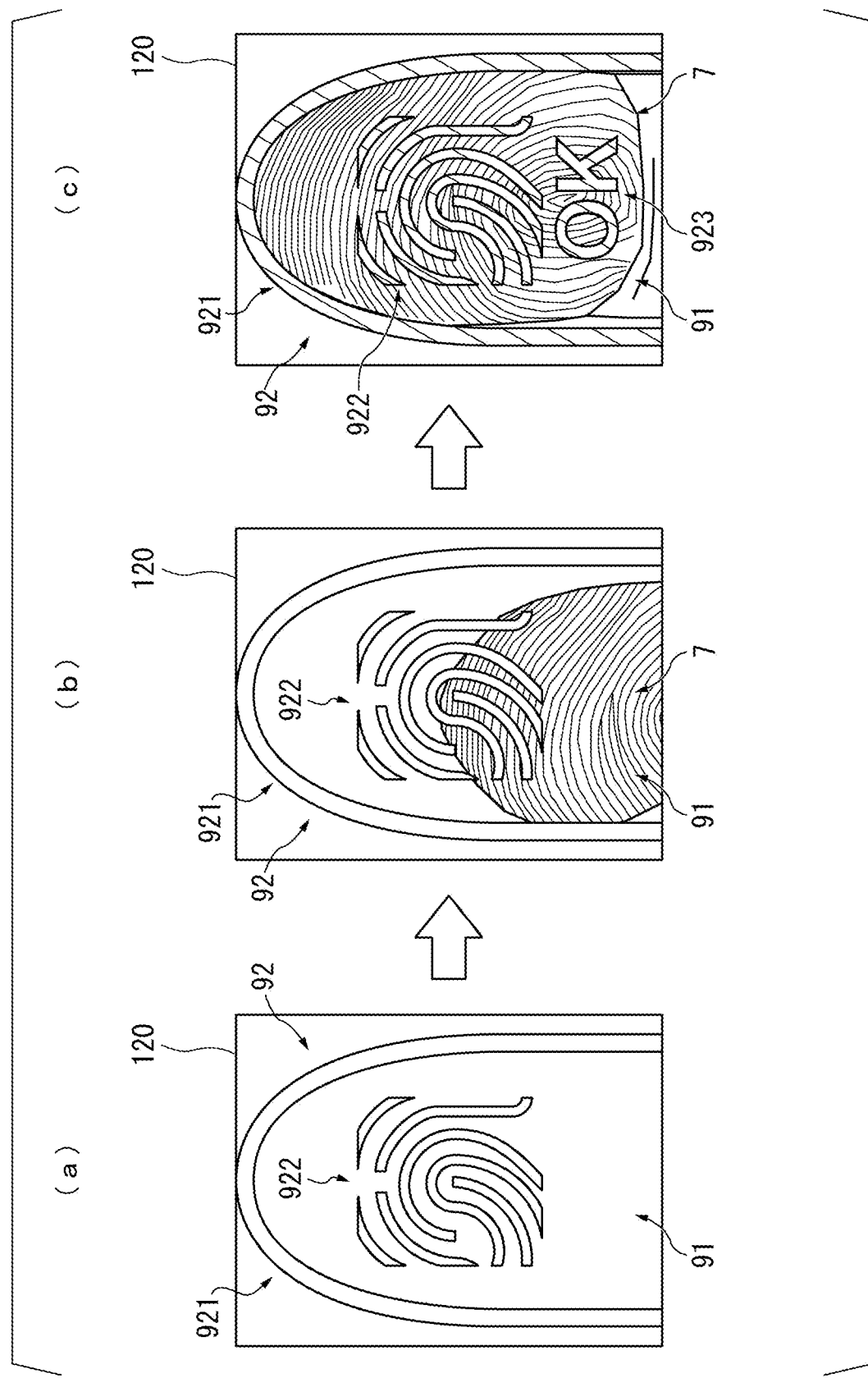
FIG. 10 is a schematic diagram for explaining an operation example of the imaging device 1 shown in FIG. 1.

Next, an operation example of the imaging device 10 described with reference to FIGS. 1 and 2 will be described with reference to FIGS. 9 and 10. FIG. 9 is a flowchart showing an operation example of the imaging device 10 shown in FIGS. 1 and 2. FIG. 10 is a schematic view showing a display example of the display portion 12 of the imaging device 10 shown in FIG. 2. Portion (a) of FIG. 10 shows the image (display state) displayed in a display area 120 when the fingertip portion 7 is not placed at the imaging position 14. Portion (b) of FIG. 10 shows the image (display state) displayed in the display area 120 when the fingertip portion 7 is placed at the imaging position 14 but the manner of placement of the fingertip portion 7 is not correct. Portion (c) of FIG. 10 shows the image (display state) displayed in the display area 120 when the fingertip portion 7 is correctly placed at the imaging position 14.

The process shown in FIG. 9 is repeatedly executed at predetermined intervals. Further, as shown in FIG. 2, when the first imaging portion 11 has the first imaging portion 11a and the first imaging portion 11b, the control portion 13 executes the process shown in FIG. 9 based on the captured image of the first imaging portion 11a and the process shown in FIG. 9 based on the captured image of the first imaging portion 11b sequentially or in parallel.

When the process shown in FIG. 9 is started, the control portion 13 acquires the first image M1 output by the first imaging portion 11 (Step S11). Next, the control portion 13 determines whether or not the fingertip portion 7, which is the object, is correctly placed at the imaging position 14 (Step S12). In Step S12, the control portion 13 determines whether or not the fingertip portion 7 is correctly placed at the imaging position 14 as follows, for example. That is, the control portion 13 first extracts the contour line of the fingertip portion 7 from the first image M1. Then, the control portion 13 determines that the fingertip portion 7 is correctly placed at the imaging position 14 when the position and orientation of the contour line are within a predetermined range. On the other hand, the control portion 13 determines that the fingertip portion 7 is not correctly placed at the imaging position 14 when the contour line of the fingertip portion 7 cannot be extracted from the first image M1 or when the position or orientation of the extracted contour line is not within the predetermined range. Alternatively, the control portion 13 may determine that the fingertip portion 7 is correctly placed when the distribution state of pixel values of the first image M1 matches a predetermined pattern, and may determine that the fingertip portion 7 is not correctly placed when not so. Alternatively, the control portion 13 may determine that the fingertip portion 7 is correctly placed when the average value or the dispersion value of the pixel values of the first image M1 is within a predetermined range, and may determine that the fingertip portion 7 is not correctly placed when not so. The value that serves as a reference for determination may be obtained, for example, experimentally or by simulation. Further, the determination in Step S12 may be executed every time in the process shown in FIG. 9, or may be executed every two or more times.

Upon having determined in Step S12 that the fingertip portion 7 is correctly placed (in the case of "YES" in Step S13), the control portion 13 displays the first display image and the second display image in the display mode for the case of the fingertip portion 7 being correctly placed (Step S14), and ends the process shown in FIG. 9. On the other hand, upon having determined in Step S12 that the fingertip portion 7 is not correctly placed (in the case of "NO" in Step S13), the control portion 13 displays the first display image and the second display image in the display mode for the case of the fingertip portion 7 not being correctly placed (Step S15), returns to Step S11, and repeats the processes of steps S11 to S13.

In Step S14 and Step S15, the control portion 13, for example, changes the display mode of the display portion 12 as follows. That is, if not placed correctly, the control portion 13 displays the first display image 91 and the second display image 92 as shown in portion (a) or portion (b) of FIG. 10. The first display image 91 is an actual image showing the state of the imaging position 14 based on the first image M1 (at least one of the second image M2 and the third image M3). In portion (a) of FIG. 10, the display area 120 does not include the image of the fingertip portion 7. In portion (b) of FIG. 10, the display area 120 includes the image of the fingertip portion 7 when not placed correctly. The second display image 92 is an image displayed superimposed on the first display image 91, and includes a contour image (guidance) 921 and a mask image 922. The contour image 921 is a pattern showing the position of the contour of the fingertip portion 7 when the fingertip portion 7 is correctly placed at the imaging position 14. In portion (a) and portion (b) of FIG. 10, the contour image 921 is, for example, displayed in red. The mask image 922 is a pattern that masks (hides) at least a part of the fingerprint, which is a physical feature portion. The mask image 922 is displayed, for example, to prevent a person other than the user of the imaging device 10 from imaging the user's fingerprint image displayed on the display portion 12. In portion (a) and portion (b) of FIG. 10, the mask image 922 is displayed, for example, in red.

When the fingertip portion 7 is correctly placed, the control portion 13 displays the first display image 91 and the second display image 92 as shown in portion (c) of FIG. 10. The second display image 92 shown in portion (c) of FIG. 10 includes the contour image 921 and the mask image 922 having the same shapes as in portion (a) and portion (b) of FIG. 10 but a different color. When the fingertip portion 7 is correctly placed, the contour image 921 and the mask image 922 are displayed in blue, for example. By the change in the color of the second display image, the user can recognize that the fingertip portion 7 is correctly placed at the imaging position 14. Moreover, the second display image 92 shown in portion (c) of FIG. 10 includes an image (display) showing that the fingertip portion 7 is correctly placed at the imaging position 14, specifically, a character image 923 expressing the character string of "OK". The character image 923 is displayed in blue, for example. The user can also recognize that the fingertip portion 7 is correctly placed at the imaging position 14 by the inclusion of the character string indicating the correctness in the second display image.

As a guide for changing this display, when confirming the placement positions of both fingers, if one of the fingers is placed correctly, the display of the corresponding finger may be changed individually. Further, a display to the effect of completion may be displayed only when both fingers are correctly placed, that is, placement of the fingers has been normally completed. With such a display, when it is necessary to authenticate the images of a plurality of fingers (parts of a living body), it is possible to more clearly determine that the necessary images have been captured without omission.

If the arrangement of the optical elements (the configuration of the optical path through which the image is transmitted) causes the captured image to be upside down or a mirror image, image processing is performed that flips the top and bottom of the captured image or inverts the mirror image as necessary.

When the first imaging portion 11 includes the second imaging portion 6 and the third imaging portion 5, and the first image M1 includes the second image M2 captured by the second imaging portion 6 and the third image M3 captured by the third imaging portion 5, as shown in FIG. 3, the display portion 12 and the control portion 13 may operate as follows. That is, in this case, the display portion 12 can display the first display image 91 representing the fingertip portion 7, which is the object, based on the second image M2. Further, the control portion 13 can determine whether or not the fingertip portion 7, which is the object, is correctly placed at the imaging position 14 based on the third image M3.

Figure 11:
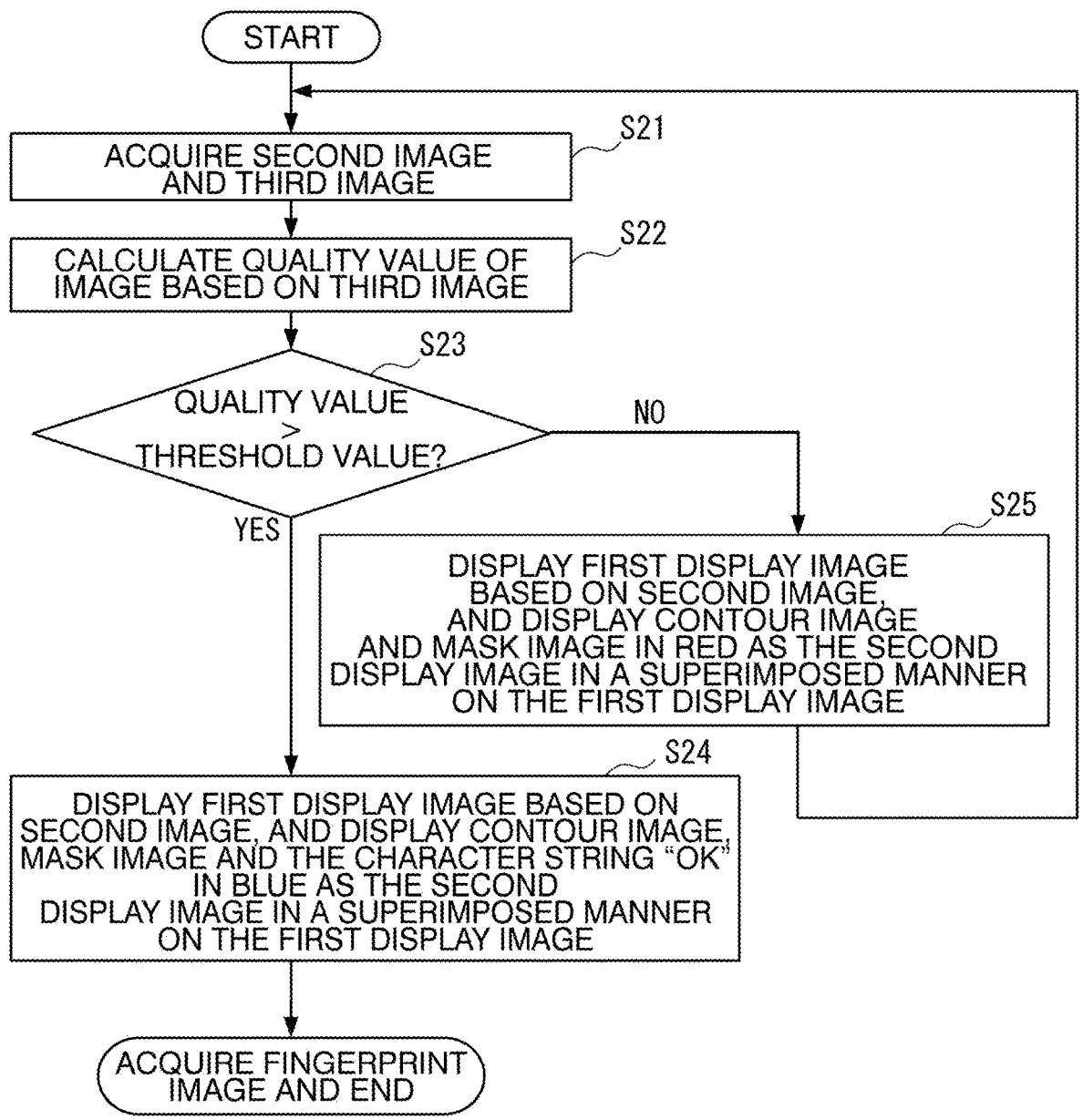
FIG. 11 is a flowchart showing another operation example of the imaging device 1 shown in FIG. 1.

Next, with reference to FIG. 11, an operation example of the imaging device 10 shown in FIGS. 1 and 2 when the imaging unit 1 is configured as shown in FIG. 3 will be described. FIG. 11 is a flowchart showing an operation example of the imaging device 10 shown in FIGS. 1 and 2 when the imaging unit 1 is configured as shown in FIG. 3. In this case, the first imaging portion 11 includes the two types of imaging portions, that is, the second imaging portion 6 and the third imaging portion 5.

The process shown in FIG. 11 is repeatedly executed at a predetermined period. When the first imaging portion 11 has the first imaging portion 11a and the first imaging portion 11b, as shown in FIG. 2, the control portion 13 executes the process shown in FIG. 11 based on the captured image and the process shown in FIG. 11 based on the captured image of the first imaging portion 11b sequentially or in parallel while displaying the captured image of the first imaging portion 11a in real time.

When the process shown in FIG. 11 is started, the control portion (determination portion) 13 acquires the second image M2 output by the second imaging portion 6 and the third image M3 output by the third imaging portion 5 (Step S21). Next, the control portion 13 calculates a quality value of the third image M3 based on the third image M3 (Step S22). However, the quality value calculation process in Step S22 may be executed every time in the process shown in FIG. 11 or may be executed every two or more times.

The quality value of the image is an index value indicating the quality of the fingerprint image for fingerprint collation. As the image quality value, for example, the NFIQ (NIST Fingerprint Image Quality) value (NIST (National Institute of Standards and Technology) Fingerprint Image Quality value (NFIQ NISTIR 7151—Fingerprint Image Quality, NIST Interagency Report, August 2004)), a quality value based on the average concentration or dispersion value described in Japanese Unexamined Patent Application, First Publication No. 2002-222424, a quality value based on the certainty of minutiae described in Japanese Unexamined Patent Application, First Publication No. 2007-226746, and the like may be used. If the quality value of the image is equal to or greater than a predetermined value, the image has sufficient quality to be used for fingerprint collation. Therefore, when the quality value of the image is equal to or greater than a predetermined value, this means that the fingertip portion 7 was imaged in a state of being correctly placed at the imaging position 14.

The image quality value is not limited to the above-mentioned quality values that evaluate the quality of the image itself. The image quality value may simply be a value indicating the degree to which the finger is placed in the correct position with respect to the guide (the contour image 921) (that is, a value that is an index of the magnitude of misalignment).

When the quality value calculated in Step S22 exceeds a predetermined threshold value (in the case of "YES" in Step S23), the control portion 13 causes the display portion 12 to display the next image (Step S24). That is, as shown in portion (c) of FIG. 10, in Step S24, the control portion 13 displays the first display image 91 based on the second image M2 and displays in blue the contour image 921, the mask image 922 and the character image 923 expressing the character string "OK" as the second display image with being superimposed on the first display image (Step S24). On the other hand, when the quality value calculated in Step S22 does not exceed a predetermined threshold value (in the case of "NO" in Step S23), the control portion 13 causes the display portion 12 to display the next image (Step S25). That is, as shown for example in portion (a) or portion (b) of FIG. 10, in Step S24 the control portion 13 displays the first display image 91 based on the second image M2 and displays in red the contour image 921 and the mask image 922 as the second display image with being superimposed on the first display image 91 (Step S25). The control portion 13 ends the process shown in FIG. 11 after the process of Step S24 or Step S25.

In actual operation, even if the finger is placed correctly, the required quality value may not be obtainable due to the state of the finger (an abnormal surface condition due to the effect of wrinkles, grime, dryness, and the like) or grime in the optical system. In such a case, repetition of collation may not be concluded, resulting in a delay of the work. For this reason, after a predetermined time has elapsed, or in the case of the process of NG (in the case of "NO" in Step S23) being repeated a predetermined number of times, it is desirable to perform a process such as a display that the fingerprint cannot be acquired, the turning on of a warning lamp, or the like. Further, instead of or in addition to the warning lamp, notification by display or audio that a clerk should be called may be made. It should be noted that this notification operation may also be performed based on the detection of some intention display (speaking or operation of the call button) by the user regardless of the number of repetitions of NG.

Note that from the viewpoint of preventing leakage of personal information due to peeping at the display screen or the like, it is desirable that the image displayed on the display portion 12 be data obtaining by transforming an image actually imaged by the first to third imaging portions 11, 5 and 6 and used for collation, or a dummy image that simply shows the outline of the fingertip portion or the like.

As this display image, for example, an image obtained by the following processes (1) to (4) can be used.

Process (1): The position of the finger is detected in real time based on the second image M2.

Process (2): The display portion 12 displays a frame serving as a guide and a diagram showing the front side of the finger as seen from the fingernail side.

Process (3): The diagram showing the front side of the finger is moved according to the position detected in Process (1).

Process (4): If the finger fits in the frame, it is determined that the fingertip portion 7 is correctly placed.

That is, the fingernail side is displayed in an animation manner, not the image of the fingerprint side of the finger. By doing so, the animation displayed on the display portion and the direction in which the actual user's finger moves can be made the same, and so better operability can be obtained.

Further, the image on the fingernail side may be displayed on the display on the user side to indicate the position, while the image on the fingerprint side may be displayed on the display on the staff side.

As described above, according to the second example embodiment, the user can easily place the fingertip portion 7, which is the object, at the correct imaging position 14.

The first and second example embodiments may be modified as in the following Modifications 1 to 5.

Modification 1

In the above example embodiment, a display (display portion 101) for allowing the user to recognize the position of the finger is provided. Further, another display may be provided so that a clerk confirming the fingerprint or the like can recognize the position of the finger. Alternatively, the image of the user's finger may be displayed by switching the screen display of the existing display used by a clerk, or on a part of a split screen. Moreover, the image may be transmitted and displayed via a wireless or wired communication path.

By visually checking the image of the finger in this way, the clerk can check the placement state of the user's finger, and it can be used for the clerk to prompt the user to move the position or monitor for fraudulent activity.

Modification 2

When the user places a finger in the vicinity of the guide, the display may be changed as follows, instead of the mode of display in the above example embodiments.

As specific examples of changing the way the guide display changes depending on the state of the finger when the finger is placed near the guide, the display may be changed as follows.

(Example a) Default color when no finger is placed within the imaging range: blue (Example b) When the finger can be confirmed on the display screen but has not reached the normal position: white (Example c) When placed normally according to the guide: red (Example d) When the contour of the finger cannot be confirmed normally: orange (Example e) In case of system error: yellow Note that the mode of change may not be the color, and a change in the display mode such as a change in shape could be notified to the user.

Modification 3

The fingerprint image may be fed back to the display and displayed in real time. In this case, from the viewpoint of preventing peeping by a third party, it is desirable to perform a predetermined process on the fingerprint image to display only a silhouette or contour of the finger.

Modification 4

The natural image of a finger acquired by a reading portion may be further transmitted to an external terminal and used for advanced determining processing such as false finger judgment. In this case, as for the external terminal, transmission may be performed to a terminal including at least one of a display or an analysis portion, with the external terminal being provided with, for example, the following functions.

(Function a) When only a display is provided, a visual judgment can be made by a clerk.

(Function b) If an analysis portion is provided, false finger determination by some algorithm is also possible.

(Function c) When a display and an analysis portion are provided, in addition to the above functions a and b, a function may be provided in which a clerk views the result of the analysis portion and makes a final judgment.

Modification 5

As the example embodiments, the case of a fingerprint image as an image including biological features has been described, but the biological feature included in the captured image is not limited thereto. For example, it may be a biological feature such as a vein, a skin pattern, or a palm print. In this case, the quality value may be a value indicating the degree to which the image including the above-mentioned biological feature is suitable for collation, in addition to the index value indicating the quality of the fingerprint image.

Although the example embodiments have been described above with reference to the accompanying drawings, the specific configuration is not limited to the above example embodiments, and includes design changes and the like within a range that does not deviate from the gist of the example embodiments.

This application is based upon and claims the benefit of priority from Japanese patent application No. 2018-218343, filed Nov. 21, 2018, the disclosure of which is incorporated herein in its entirety by reference.

INDUSTRIAL APPLICABILITY

The example embodiments may be applied to an imaging device and an imaging method.

REFERENCE SYMBOLS

1: Imaging unit
2: First light source portion
2a to 2d: Visible light LED
3: Second light source portion
3a to 3h: Infrared LED
4: Optical element (prism)
4a: Contact surface
4b: Intersecting surface
4c: Opposing surface
5: Third imaging portion
6: Second imaging portion
10: Imaging device
11, 11a, 11b: First imaging portion
12: Display portion
13: Control portion
14 14a, 14b: Imaging position
15: Determination portion
91: First display image
92: Second display image
921: Contour image
922: Mask image
923: Character image
L1: First light
L2: Second light

What is claimed is:

1. An imaging device comprising:
a camera that captures an image of a portion of a living body;
a display that displays a first display image and a second display image superimposed on each other, the first display image based on the image captured by the camera, the second display image including guidance for placing the portion of the living body in a prescribed position, the display displaying a contour image as the guidance;
at least one memory configured to store instructions; and
at least one processor configured execute the instructions to:
determine whether the portion of the living body is placed in the prescribed position;
until the portion of the living body has been determined as being placed in the prescribed position, cause the camera to recapture the image of the portion of the living body and cause the display to display the first display image based on the image recaptured by the camera;
cause the display to display the contour image in a first color when the portion of the living body is not placed in the prescribed position; and
cause the display to display the contour image in a second color different than the first color when the portion of the living body is placed in the prescribed position,
wherein the portion of the living body includes a physical feature portion for biometric authentication,
the second display image includes a mask image that masks at least a part of the physical feature portion, and the mask image comprises one or more mask portions, each mask portion defining an opaque area such that in a superimposition of the first and second display images on each other, the physical feature portion is not visible within the opaque area.

2. The imaging device according to claim 1, wherein determining whether the portion of the living body is placed in the prescribed position comprises determining that the portion of the living body is placed at the prescribed position when a quality value of the image captured by the camera is equal to or greater than a predetermined threshold value.

3. The imaging device according to claim 2, wherein the first display image is an image in which an infrared component is removed.

4. The imaging device according to claim 1, wherein the portion of the living body is a fingertip portion.

5. An imaging method comprising:
capturing an image of a portion of a living body;
displaying a first display image and a second display image superimposed on each other, the first display image based on the captured image, the second display image including guidance for placing the portion of the living body in a prescribed position, a contour image being displayed as the guidance;
determining whether the portion of the living body is placed in the prescribed position;
until the portion of the living body has been determined as being placed in the prescribed position, recapturing the image of the portion of the living body and displaying the first display image based on the recaptured image,
wherein the contour image is displayed in a first color when the portion of the living body is not placed in the prescribed position,
the contour image is displayed in a second color that is different from the first color when the portion of the living body is placed in the prescribed position,
the portion of the living body includes a physical feature portion for biometric authentication,
the second display image includes a mask image that masks at least a part of the physical feature portion, and
the mask image comprises one or more mask portions, each mask portion defining an opaque area such that in a superimposition of the first and second display images on each other, the physical feature portion is not visible within the opaque area.

* * * * *